US009393048B2

(12) United States Patent
Carbone et al.

(10) Patent No.: US 9,393,048 B2
(45) Date of Patent: Jul. 19, 2016

(54) POLYAXIAL BONESCREW ASSEMBLY

(75) Inventors: John Carbone, Lutherville, MD (US); Oheneba Boachie-Adjei, Briarcliff, NY (US); Larry McClintock, Gore, VA (US); Kevin R. Strauss, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 27 days.

(21) Appl. No.: 13/580,746

(22) PCT Filed: Feb. 23, 2011

(86) PCT No.: PCT/US2011/025801
§ 371 (c)(1),
(2), (4) Date: Sep. 26, 2012

(87) PCT Pub. No.: WO2011/106339
PCT Pub. Date: Sep. 1, 2011

(65) Prior Publication Data
US 2013/0013003 A1    Jan. 10, 2013

Related U.S. Application Data

(60) Provisional application No. 61/307,055, filed on Feb. 23, 2010, provisional application No. 61/310,056, filed on Mar. 3, 2010.

(51) Int. Cl.
*A61B 17/70* (2006.01)
*A61B 17/86* (2006.01)

(52) U.S. Cl.
CPC .......... *A61B 17/7037* (2013.01); *A61B 17/7032* (2013.01); *A61B 17/863* (2013.01); *A61B 17/7004* (2013.01)

(58) Field of Classification Search
CPC .......................... A61B 17/70–17/7013; A61B 17/7035–17/704
USPC .......... 606/246, 259–278, 300, 308, 315–317
See application file for complete search history.

(56) References Cited

U.S. PATENT DOCUMENTS 5,885,286 A    3/1999    Sherman et al.
5,964,760 A    10/1999    Richelsoph
(Continued)

FOREIGN PATENT DOCUMENTS

EP    1634537 A1    3/2006
EP    1774919 A1    4/2007
(Continued)

OTHER PUBLICATIONS

International Search Report PCT/US2011/025801 dated Apr. 15, 2011.

*Primary Examiner* — Eduardo C Robert
*Assistant Examiner* — Michelle C Eckman
(74) *Attorney, Agent, or Firm* — Carter, DeLuca, Farrell & Schmidt, LLP

(57) ABSTRACT

A bone screw assembly includes a screw, an outer housing, and an inner housing. The screw includes a shank and a head. The outer housing has a proximal end, a distal end, and a passageway extending longitudinally therethrough. The outer housing defines a saddle at the proximal end thereof for receiving at least a portion of a rod therein. The inner housing is positionable within the passageway of the outer housing. The inner housing has a recessed distal portion for receiving the head of the screw therein. The inner housing also includes a proximal surface defining a substantially V-shaped configuration for receiving rods of different diameters therein.

17 Claims, 11 Drawing Sheets

(56) References Cited

U.S. PATENT DOCUMENTS

| | | | |
|---|---|---|---|
| 6,074,393 A | 6/2000 | Sitoto | |
| 6,355,040 B1 | 3/2002 | Richelsoph et al. | |
| 6,402,752 B2 | 6/2002 | Schaffler-Wachter et al. | |
| 6,485,491 B1 | 11/2002 | Farris et al. | |
| 6,565,569 B1 | 5/2003 | Assaker et al. | |
| 6,872,209 B2 | 3/2005 | Morrison | |
| 6,875,211 B2 | 4/2005 | Nichols et al. | |
| 6,881,215 B2 | 4/2005 | Assaker et al. | |
| 7,128,743 B2 | 10/2006 | Metz-Stavenhagen | |
| 7,144,396 B2 | 12/2006 | Shluzas | |
| 7,211,086 B2 | 5/2007 | Biedermann et al. | |
| 7,857,834 B2* | 12/2010 | Boschert | 606/269 |
| 7,935,135 B2* | 5/2011 | Mujwid | 606/266 |
| 2005/0203516 A1* | 9/2005 | Biedermann et al. | 606/61 |
| 2005/0277928 A1* | 12/2005 | Boschert | 606/61 |
| 2006/0089643 A1* | 4/2006 | Mujwid | 606/61 |
| 2006/0111715 A1 | 5/2006 | Jackson | |
| 2006/0200131 A1 | 9/2006 | Chao et al. | |
| 2006/0241769 A1 | 10/2006 | Gordon et al. | |
| 2006/0276789 A1* | 12/2006 | Jackson | 606/61 |
| 2007/0118123 A1* | 5/2007 | Strausbaugh | A61B 17/7032 606/272 |
| 2008/0039844 A1* | 2/2008 | Jackson | 606/61 |
| 2008/0091213 A1 | 4/2008 | Jackson | |
| 2009/0005814 A1 | 1/2009 | Miller et al. | |
| 2009/0105716 A1 | 4/2009 | Barrus | |
| 2009/0105769 A1 | 4/2009 | Rock et al. | |
| 2009/0149887 A1* | 6/2009 | Schlaepfer | A61B 17/7034 606/278 |
| 2009/0163956 A1* | 6/2009 | Biedermann et al. | 606/265 |
| 2009/0163962 A1* | 6/2009 | Dauster | A61B 17/7032 606/305 |
| 2009/0182384 A1* | 7/2009 | Wilcox | A61B 17/7032 606/305 |
| 2009/0216280 A1* | 8/2009 | Hutchinson | 606/279 |
| 2009/0228053 A1 | 9/2009 | Kolb et al. | |
| 2009/0299414 A1* | 12/2009 | Jackson | 606/301 |
| 2009/0318970 A1* | 12/2009 | Butler et al. | 606/264 |
| 2010/0023061 A1* | 1/2010 | Randol et al. | 606/278 |
| 2010/0063544 A1* | 3/2010 | Butler | 606/261 |
| 2010/0114170 A1* | 5/2010 | Barrus et al. | 606/264 |
| 2010/0114171 A1 | 5/2010 | Boachie-Adjei et al. | |
| 2010/0137918 A1* | 6/2010 | Wilcox et al. | 606/301 |
| 2010/0160978 A1 | 6/2010 | Carbone | |
| 2010/0160980 A1* | 6/2010 | Walsh et al. | 606/308 |
| 2010/0179602 A1* | 7/2010 | Dauster et al. | 606/308 |
| 2010/0234902 A1* | 9/2010 | Biedermann | A61B 17/7037 606/305 |
| 2010/0286731 A1* | 11/2010 | Biedermann et al. | 606/264 |
| 2011/0093021 A1* | 4/2011 | Fanger | A61B 17/7037 606/308 |
| 2011/0098756 A1* | 4/2011 | Brannon | 606/309 |
| 2011/0251650 A1* | 10/2011 | Biedermann et al. | 606/305 |
| 2011/0257686 A1* | 10/2011 | Metcalf et al. | 606/264 |
| 2011/0276095 A1* | 11/2011 | Bar | A61B 17/863 606/279 |
| 2011/0307014 A1* | 12/2011 | Niinomi et al. | 606/264 |
| 2012/0035666 A1* | 2/2012 | Ladd et al. | 606/301 |
| 2012/0165874 A1* | 6/2012 | Biedermann et al. | 606/278 |
| 2012/0179210 A1* | 7/2012 | Garamszegi | 606/305 |
| 2012/0209335 A1* | 8/2012 | Termyna et al. | 606/300 |
| 2013/0046345 A1* | 2/2013 | Jones et al. | 606/266 |
| 2013/0096616 A1* | 4/2013 | Dickinson | 606/264 |
| 2013/0103094 A1* | 4/2013 | Beale et al. | 606/279 |

FOREIGN PATENT DOCUMENTS

| | | |
|---|---|---|
| EP | 2052690 A1 | 4/2009 |
| WO | 2009/015100 A2 | 1/2009 |
| WO | 2010077284 A1 | 7/2010 |

* cited by examiner

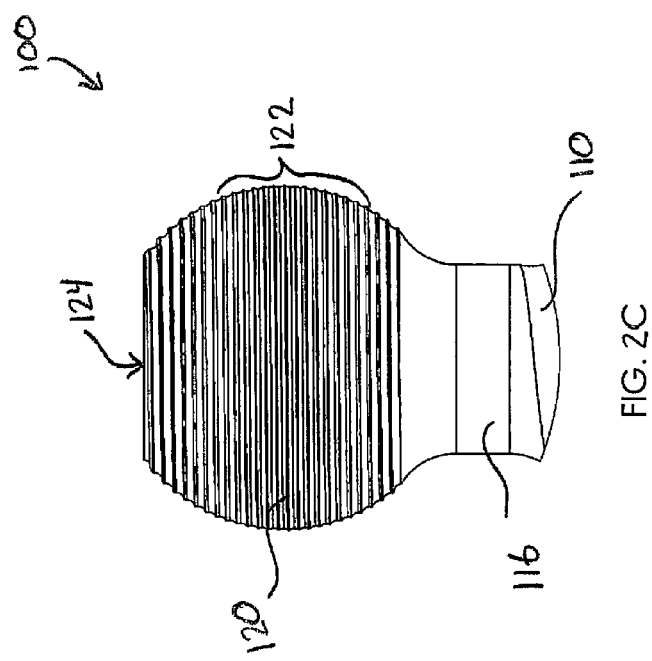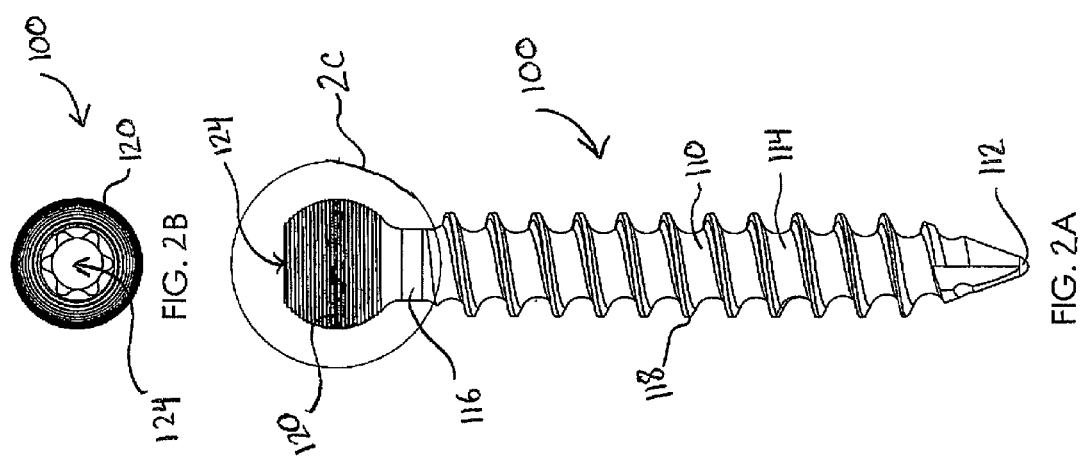

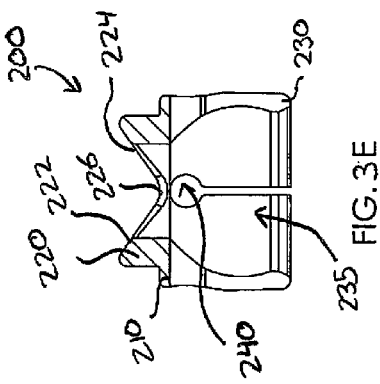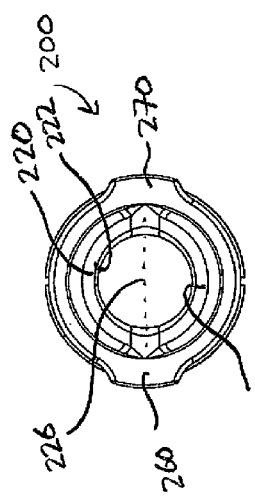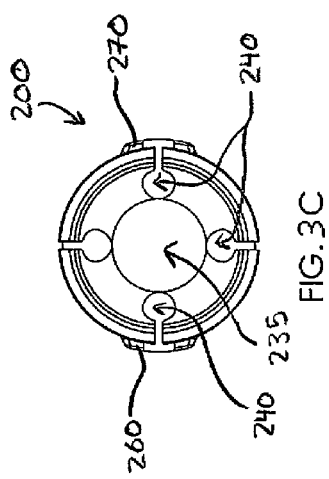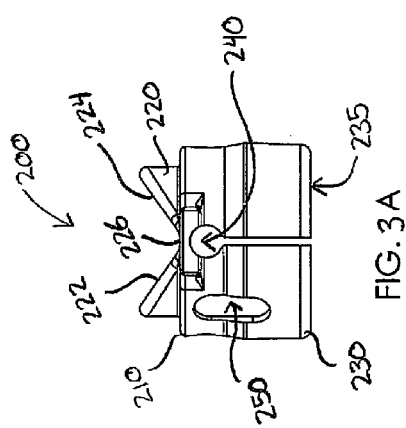

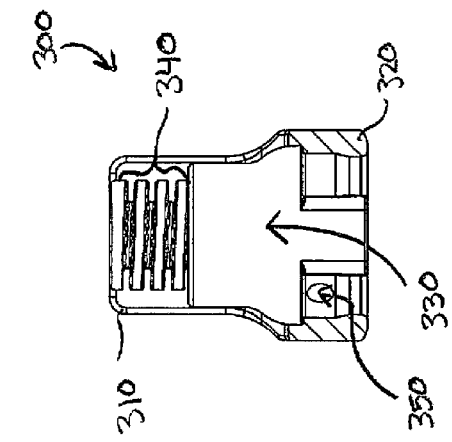
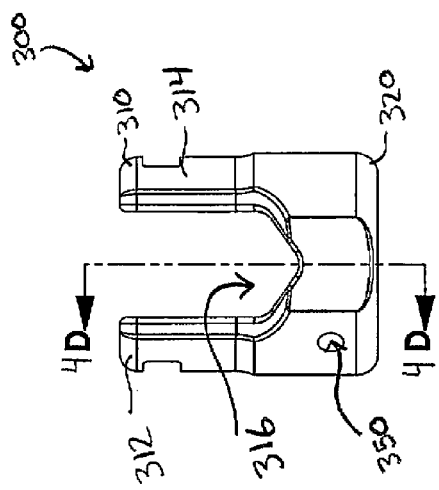
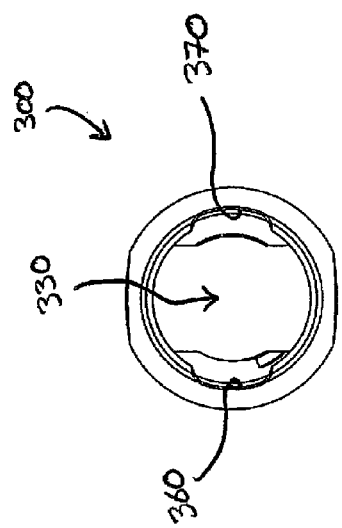
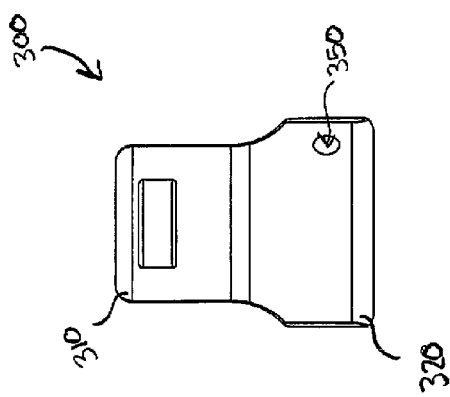
FIG. 4D
FIG. 4B
FIG. 4C
FIG. 4A

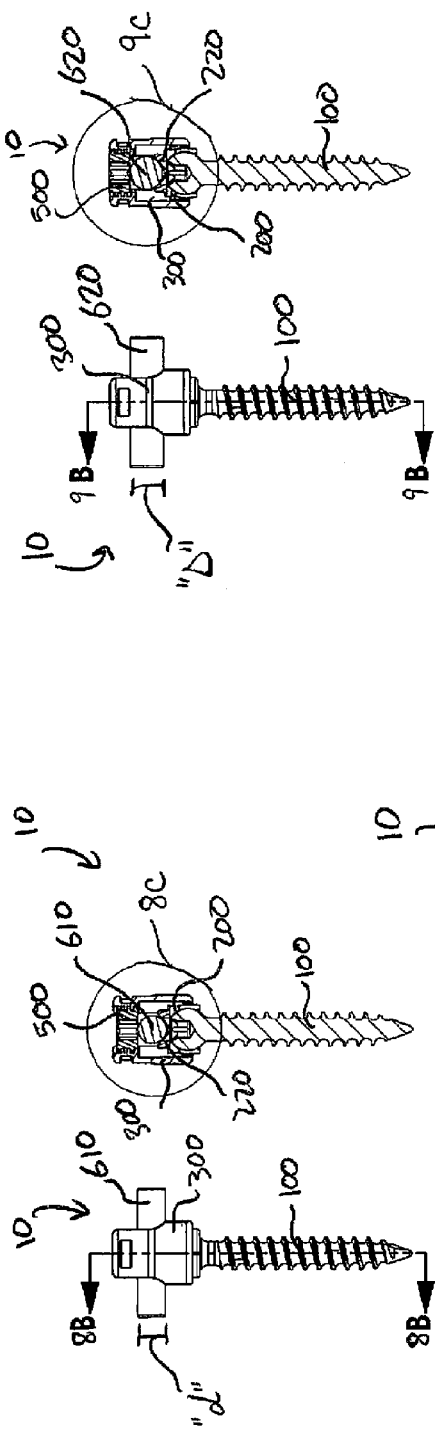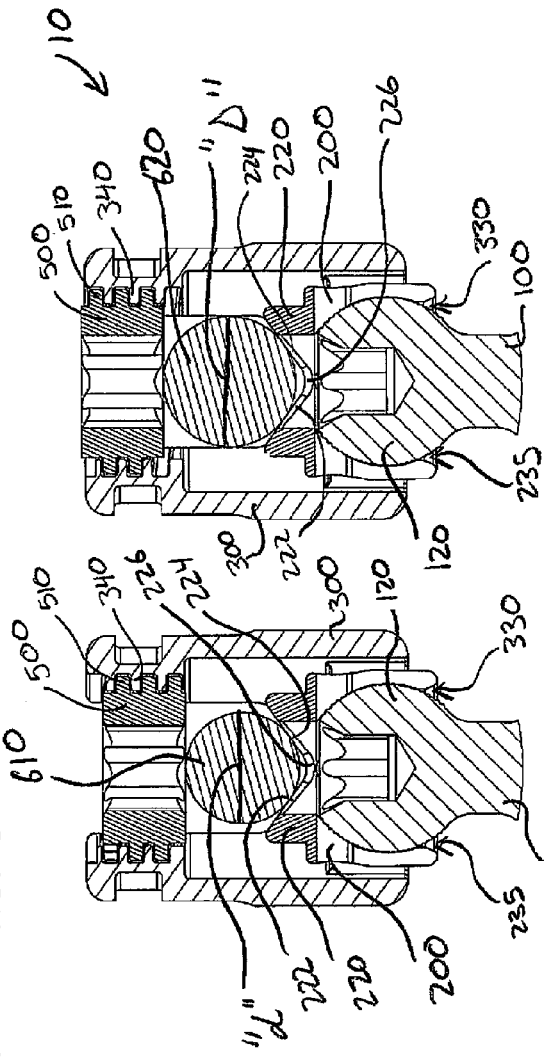

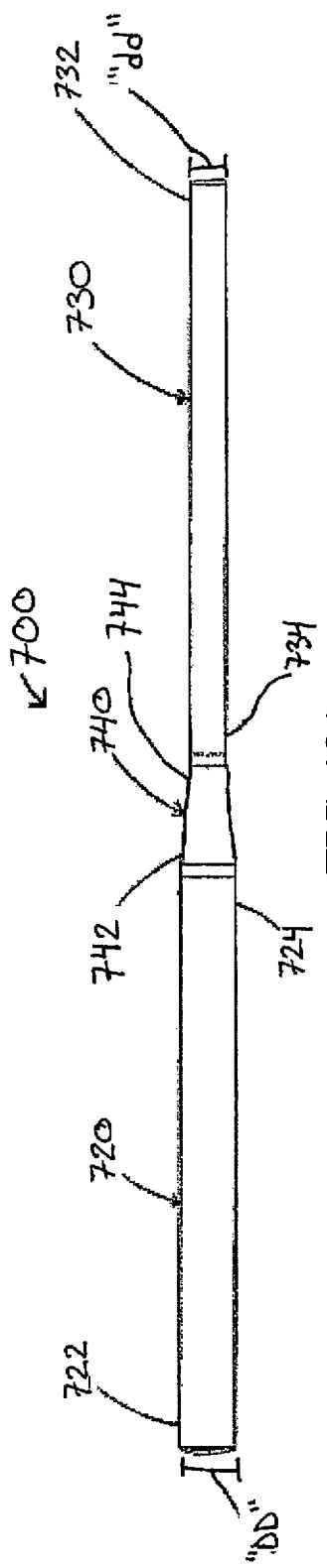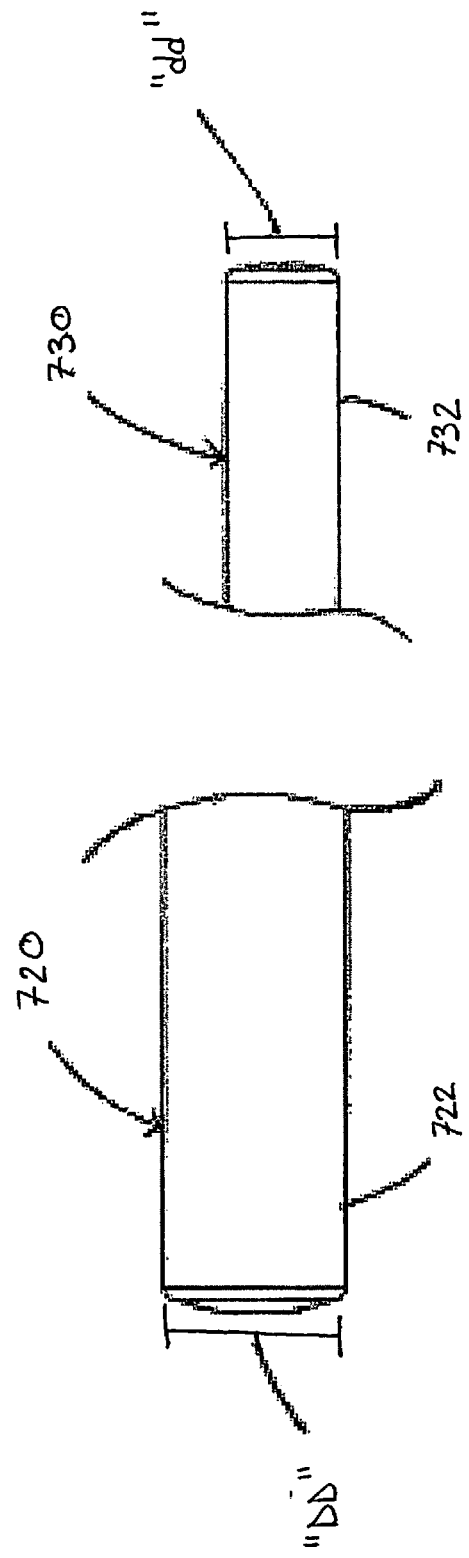
FIG. 10A
FIG. 10B
FIG. 10C

POLYAXIAL BONESCREW ASSEMBLY

CROSS-REFERENCE TO RELATED APPLICATIONS

This application is a U.S. National Stage Application filed under 35 U.S.C. §371(a) of International Application No. PCT/US2011/025801 filed on Feb. 23, 2011, which claims the benefit of, and priority to, U.S. Provisional Patent Application Ser. No. 61/307,055 filed on Feb. 23, 2010, and U.S. Provisional Patent Application Ser. No. 61/310,056 filed on Mar. 3, 2010, the entire contents of which are incorporated by reference herein.

BACKGROUND

1. Technical Field

The present disclosure relates bone anchors and, more particularly, to bone screw assemblies for use with surgical rods of varying diameter.

2. Background of Related Art

The adult human spinal column has 24 vertebrae coupled to one another by a tri-joint complex consisting of an anterior disc and the two posterior facet joints. The bones of the spinal column are anatomically categorized as being members of one of four classifications: cervical, thoracic, lumbar, or sacral. The cervical portion of the spine is the top of the spine and includes the first seven vertebrae beginning at the base of the skull. The next twelve bones are the thoracic vertebrae. Thereafter, the next five bones form the lumbar vertebrae. Connecting to the lumbar vertebrae is the sacral bones, including the coccyx.

The spine is a highly flexible structure, capable of a high degree of translation and rotation about all three axes. Genetic or developmental irregularities, trauma, tumors, and disease, however, can result in spinal pathologies that limit the range of motion of the spine and/or threaten the critical elements of the nervous system housed within the spinal column.

Spinal fixation apparatuses, such as bone screws and rods, are widely employed in surgical procedures for correcting spinal injuries and diseases. Depending on the pathology and treatment, a surgeon will select the appropriate spinal rod for the particular procedure, e.g., the surgeon will select a spinal rod made from a specific material and/or having a specific cross-sectional diameter. The most common rod materials include titanium (e.g., Ti-CP) and its alloys (e.g., Ti-6Al-4V), cobalt-chrome alloy (CoCr), and stainless steel (SS). Rod diameters generally range from about 3.5 mm to about 7.0 mm. Typically, the selected spinal rod is then matched to a specific bone screw (or bone screws) according to the specific configuration of the selected spinal rod, e.g., the materials and/or cross-sectional diameter of the rod.

During implantation and fixation, the bone screws are first implanted into the respective vertebrae. Thereafter, the spinal rod is secured within each of the bone screws. However, unforeseen conditions, complications, or other intra-operative events may dictate a change in the previously selected spinal rod, e.g., a different diametered rod may be desired. As can be appreciated, removing the previously implanted bone screws is undesirable. Further, it may be desirable, in some procedures, to use a spinal rod having a different diameter along its length, e.g., a tapered rod. Thus, a need exists for a bone screw assembly capable of receiving spinal rods of different diameters and/or made from different materials.

SUMMARY

In accordance with one embodiment of the present disclosure, a bone screw assembly is provided. The bone screw assembly generally includes a screw, an outer housing, and an inner housing. The screw has a shank and a head. The outer housing has a proximal end, a distal end, and a passageway extending longitudinally therethrough. The outer housing defines a saddle at the proximal end thereof that is configured to receive at least a portion of a surgical rod therein. The inner housing is positionable within the passageway of the outer housing and includes a recessed distal portion configured to receive the head of the screw therein. The inner housing also including a proximal surface defining a substantially V-shaped configuration for receiving rods of different diameters therein, e.g., rods having diameters in the range of about 3.5 mm to about 7 mm, although other ranges are also contemplated.

In one embodiment, the inner housing is moveable relative to the outer housing from a proximal position to a distal position to lock the outer housing, the inner housing, and the head of the screw in position relative to one another.

In another embodiment, a set screw is provided. The set screw is threadingly engageable with the outer housing and is configured to secure the rod within the saddle of the outer housing between the set screw and the substantially V-shaped proximal surface of the inner housing. Further, the bone screw assembly may be configured such that, as the set screw is threadingly engaged within the outer housing, the inner housing is moved relative to the outer housing from the proximal position to the distal position to lock the outer housing, the inner housing, and the head of the screw in position relative to one another.

In another embodiment, the set screw includes machined-threading disposed about an outer periphery thereof. The threading of the set screw is configured to engage threading disposed on an inner surface of the outer housing.

In yet another embodiment, a height of the set screw is selected in accordance with the diameter of the rod. More specifically, a set screw having a particular height is chosen in accordance with the rod to be used therewith such that, in a fully engaged position, a proximal surface of the set screw is substantially flush with the proximal end of the outer housing.

In still yet another embodiment, the screw, the outer housing and/or the inner housing are formed from different materials. For example, the outer housing may be formed from cobalt chrome and the inner housing and/or the screw may be formed from a different material. Further, the screw may be made from titanium, or any other material that is softer than the material making up the outer housing and/or the inner housing.

In another embodiment, a pin is provided. The pin is configured to engage both the outer housing and the inner housing to secure the outer housing and the inner housing to one another.

In yet another embodiment, the recessed distal portion of the inner housing includes a plurality of relief features defined therein. The relief features are configured to permit the recessed distal portion of the inner housing to contract upon insertion into the outer housing and to expand upon insertion of the head of the screw therein.

In still another embodiment, the head of the screw includes a plurality of circumferential ridges disposed thereon. The ridges, as can be appreciated, are configured to facilitate retention of the head of the screw within the recessed distal portion of the inner housing.

In another embodiment, the shank of the bone screw is double-threaded. More specifically, a pitch of the double-threaded shank may be in the range of about 1 mm to about 3 mm, preferably about 2 mm, while a lead of the double-threaded shank may be in the range of about 2 mm to about 6 mm, preferably about 4 mm.

BRIEF DESCRIPTION OF THE DRAWINGS

Embodiments of the presently disclosed bone screw assembly are described herein with reference to the accompanying drawings, wherein:

FIG. 2A is a side view of the bone screw of the bone screw assembly of FIG. 1A;

FIG. 2B is a top view of the bone screw of FIG. 2A;

FIG. 2C is an enlarged view of the area of detail of FIG. 2A;

FIG. 3A is a side view of the inner housing of the bone screw assembly of FIG. 1A;

FIG. 3B is a front view of the inner housing of FIG. 3A;

FIG. 3C is a bottom view of the inner housing of FIG. 3A;

FIG. 3D is a top view of the inner housing of FIG. 3A;

FIG. 3E is a longitudinal, cross-sectional view of the inner housing taken across section line 3E-3E of FIG. 3B;

FIG. 4A is a side view of the outer housing of the bone screw assembly of FIG. 1A;

FIG. 4B is a front view of the outer housing of FIG. 4A;

FIG. 4C is a top view of the outer housing of FIG. 4A;

FIG. 4D is a longitudinal, cross-sectional view of the outer housing taken across section line 4D-4D of FIG. 4B;

FIG. 8A is a side view of the bone screw assembly of FIG. 1A having a surgical rod of a first diameter coupled thereto;

FIG. 8B is a longitudinal, cross-sectional view of the bone screw assembly of FIG. 8A taken across section line 8B-8B of FIG. 8A;

FIG. 8C is an enlarged view of the area of detail of FIG. 8B;

FIG. 9A is a side view of the bone screw assembly of FIG. 1A having a surgical rod of a second diameter coupled to the bone screw assembly;

FIG. 9B is a longitudinal, cross-sectional view of the bone screw assembly of FIG. 9A taken across section line 9B-9B of FIG. 9A;

FIG. 9C is an enlarged view of the area of detail of FIG. 9B; and

FIG. 10A is a side view of a tapered surgical rod for use with the bone screw assembly of FIG. 1A;

FIG. 10B is an enlarged, side view of a first section of the tapered rod of FIG. 10A;

FIG. 10C is an enlarged, side view of a second section of the tapered rod of FIG. 10A.

DETAILED DESCRIPTION

Figure 1C:
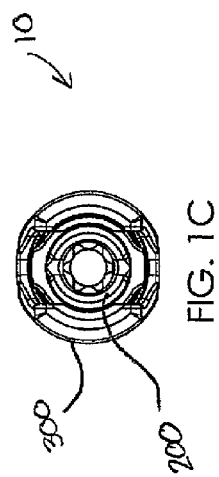
FIG. 1C is a top view of the bone screw assembly of FIG. 1A.

Various embodiments of the presently disclosed spinal fixation devices and systems will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

Figure 1B:
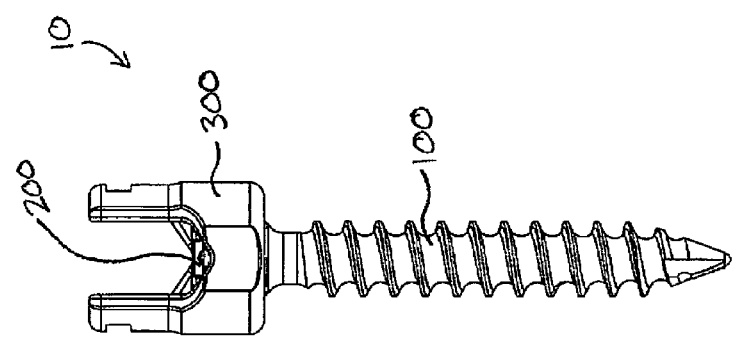
FIG. 1B is a front view of the bone screw assembly of FIG. 1A.
Figure 1A:
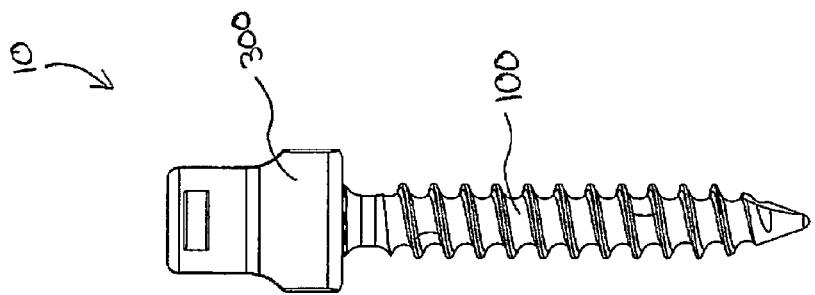
FIG. 1A is a side view of a bone screw assembly according to an embodiment of the present disclosure.
Figure 7B:
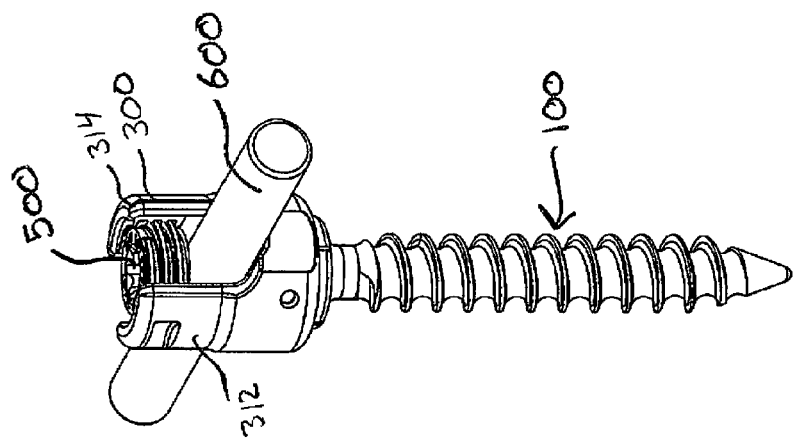
FIG. 7B is a perspective view of the bone screw assembly of FIG. 7A wherein the surgical rod is coupled to the bone screw assembly.
Figure 7A:
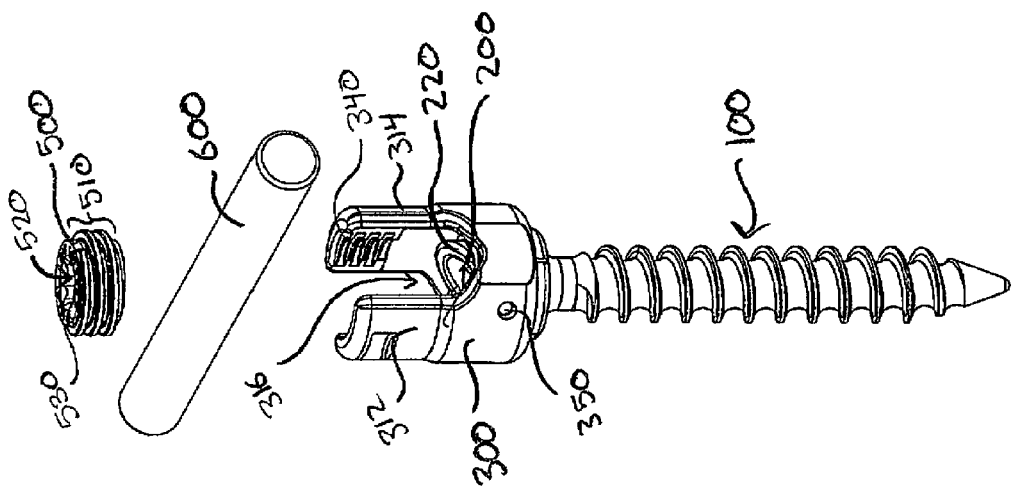
FIG. 7A is a perspective view of the bone screw assembly of FIG. 1A configured to receive a surgical rod.

Referring initially to FIGS. 1A-1C, a bone screw assembly provided in accordance with one embodiment of the present disclosure is shown identified by reference numeral 10. Bone screw assembly 10 generally includes a bone screw 100, an inner housing 200, an outer housing 300, a pin 400 (FIGS. 5A-5D), and a set screw 500 (FIGS. 7A-7B). Bone screw 100 is configured for implantation in bone. Inner housing 200 and outer housing 300 are securable to bone screw 100 and are configured to retain at least a portion of a surgical rod 600 (FIGS. 7A-7B) therein. Set screw 500 (FIGS. 7A-7B) is engageable with outer housing 300 to secure surgical rod 600 (FIGS. 7A-7B) within outer housing 300 between inner housing 200 and set screw 500 (FIGS. 7A-7B). The specific features, installation, and use of bone screw assembly 10 will be described in greater detail hereinbelow.

Turning now to FIGS. 2A-2C, bone screw 100 of bone screw assembly 10 is shown including a shank 110 and a head 120. Shank 110 includes a distal tip portion 112, an elongated body portion 114, and a proximal end 116 that is coupled to head 120, e.g., monolithically formed therewith. Distal tip portion 112 is generally conically-shaped to facilitate insertion of bone screw 100 into bone. More specifically, the distal tip portion 112 of bone screw 100 may be self-tapping, or self-starting, to facilitate insertion into bone. Elongated body portion 114 of shank 110 has a substantially uniform outer diameter and includes a continuous helical thread 118 of substantially uniform pitch formed thereon to allow for threaded insertion and retention of bone screw 100 within bone. Thread 118 disposed about elongated body portion 114 of shank 110 may be single threaded, double threaded, or otherwise configured to facilitate insertion into and fixation within bone.

Figure 11:
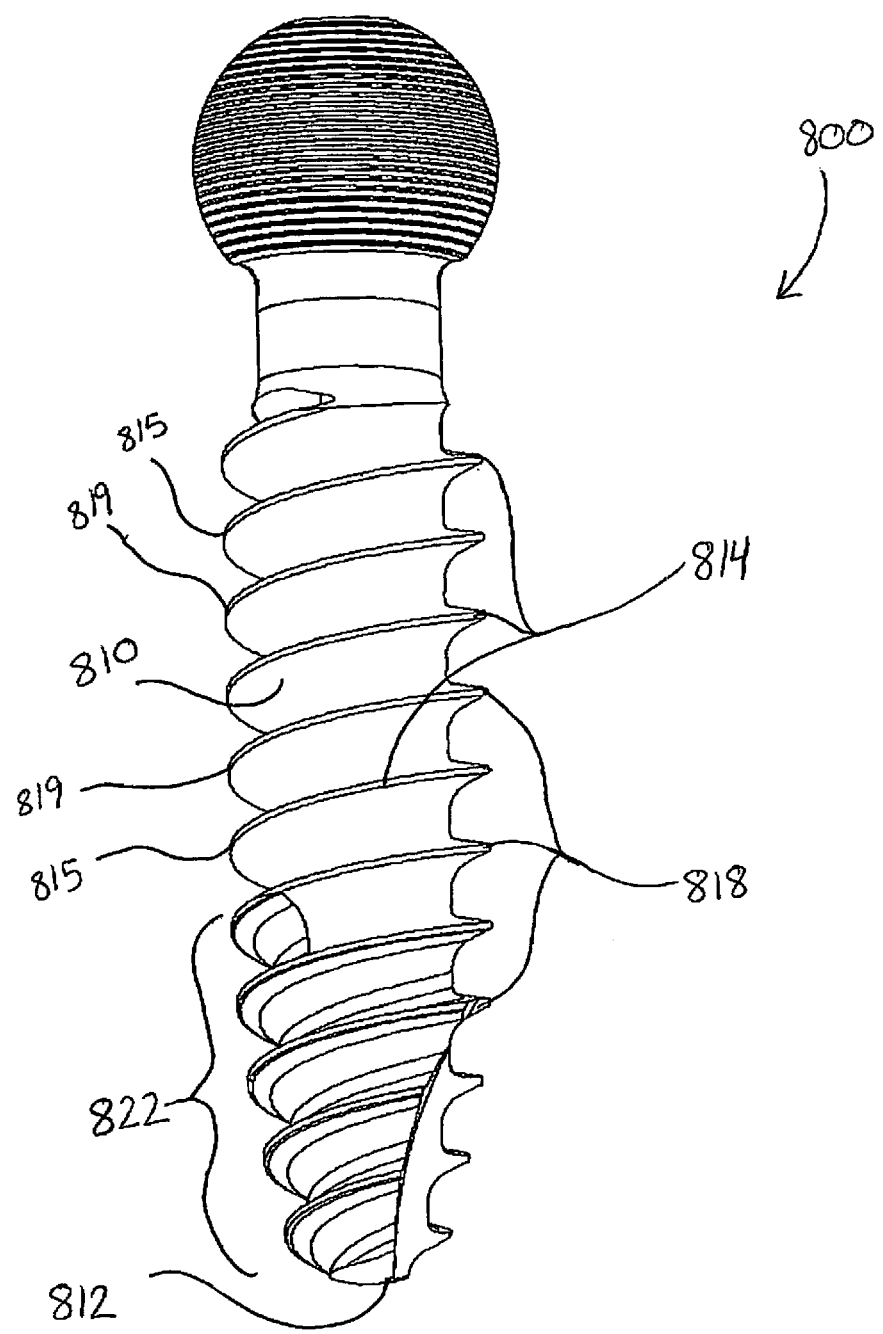
FIG. 11 is a side view of another embodiment of a bone screw provided in accordance with the present disclosure.

In an exemplary embodiment, as shown in FIG. 11, shank 810 of bone screw 800 is double-threaded, or double-lead, i.e., shank 810 includes first and second helical threads 814, 818, respectively that are offset by 180°. In this double-threaded configuration, the lead of threads 814, 818 is approximately equal to double the pitch of threads 814, 818, respectively. In other words, the axial distance that screw 800 travels during one full 360 degree rotation is approximately double the distance between adjacent crests 815, 819 of threads 814, 818, respectively. The lead of double-threaded shank 810 may be in the range of about 1 mm to about 3 mm, preferably about 2 mm, while the pitch of each of the threads 814, 818 may be in the range of about 2 mm to about 6 mm, preferably about 4 mm. Thus, while the adjacent crests 814, 818 are only about 2 mm apart from one another, the screw 800 travels a distance of about 4 mm per revolution. Further, as shown in FIG. 11, a portion 822 of shank 810 may taper distally along shank 810, eventually reaching distal tip 812 of shank 810. Specifically, both the inner and outer diameters of shank 810 may taper distally, e.g., shank 810 as well as threads 814, 818 may taper distally. Threads 814, 818 of shank 810 of bone screw 800 may also extend substantially completely to the distal tip 812 of shank 810, e.g., such that two starts (not specifically shown), one for each of the threads 814, 818, are disposed at distal tip 812 of shank 810 to facilitate insertion of screw 800 into and fixation within bone. Additionally, shank 110 (or shank 810 of bone screw 800) may be cannulated to permit passage of a guide wire (not shown) or other instrumentation therethrough.

With continued reference to FIGS. 2A-2C, head 120 of bone screw 100 is generally spherical in shape and includes a plurality of circumferentially disposed ridges 122 thereon. The spherical-shaped head 120 of bone screw 100 allows for polyaxial rotational motion of inner and outer housings 200, 300, respectively, relative to bone screw 100. Ridges 122, on the other hand, facilitate retention of head 120 of bone screw within distal recess 235 of inner housing 200 (see FIGS. 3A-3E), as will be described below. Head 120 of bone screw 100 further includes a recessed proximal portion 124. Recessed proximal portion 124 of head 120 defines a specific configuration, e.g., a six-point star configuration, or other suitable configuration, shaped complementary to a distal end of a drive tool (not shown) to permit the drive tool (not shown) to be coupled to bone screw 100 for implanting bone screw 100 within bone. It is contemplated that the head 120 be formed from a different material than shank 110 such that bone screw 100 is formed from mixed metals/alloys. Examples of suitable materials include titanium (e.g., commercially pure titanium), titanium alloys (e.g., Ti-6Al-4V), stainless steel, and cobalt chrome alloys. By way of example only, head 120 may be formed of titanium alloy and shank 110 may be formed of commercially pure titanium, or head 120 and shank 110 of bone screw 100 may both be formed from titanium or titanium alloy.

Referring now to FIGS. 3A-3E, inner housing 200 is shown. Inner housing 200 includes a proximal end 210 having a substantially V-shaped hub 220 disposed thereon and a distal end 230 defining a semi-spherical recess 235. V-shaped hub 220 of inner housing 200 extends from proximal end 210 of inner housing 200 and includes first and second angled surfaces 222, 224, respectively, that cooperate to define a nadir 226 at the base of V-shaped hub 220. It is envisioned that nadir 226 be generally centrally disposed relative to inner housing 200 and that first and second angled surfaces 222, 224 define substantially similar and uniform slopes. As will be described in greater detail below, V-shaped hub 220 is configured to seat surgical rods, e.g., rod 610 (FIGS. 8A-C) or rod 620 (FIGS. 9A-C), of varying diameters therein, or a rod 700 (FIGS. 10A-10C) having a differing diameter, e.g., a rod 700 (FIGS. 10A-10C) having a tapered configuration. More specifically, V-shaped hub 220 is configured to retain rods 610, 620 (FIGS. 8A-8C, FIGS. 9A-9C, respectively) of varying diameter, e.g., from about 3.5 mm to about 7 mm, in a stable, centered position relative to inner housing 200.

With continued reference to FIGS. 3A-3E, semi-spherical recess 235 formed within distal end 230 of inner housing 200 defines a diameter approximately equal to that of head 120 of bone screw 100 (See FIGS. 2A-2C). A plurality of slits, or relief features 240 are defined within inner housing 200 adjacent recess 235 to permit inner housing 200 to resiliently flex, e.g., allowing the dimensions of recess 235 to be expanded and contracted, such that recess 235 of inner housing 200 is capable of receiving and retaining a substantial portion of head 120 of bone screw 100 therein and such that inner housing 200 may be inserted distally into outer housing 300 (FIGS. 1A-1B). Inner housing 200 also includes a longitudinal slot 250 defined therein. Slot 250, as will be described in greater detail below, is configured to receive pin 400 (FIGS. 5A-5D) to facilitate securing of inner hosing 200 and outer housing 300 (FIGS. 1A-1B) to one another. Further, inner housing 200 includes a pair of outwardly-extending flanges 260, 270 extending outwardly from the proximal end 210 thereof. Flanges 260, 270, as will be described below, are configured to engage shelves 360, 370 defined within longitudinal passageway 330 of outer housing 300 (FIGS. 4A-4D), to inhibit rotation of inner housing 200 relative to outer housing 300 when disposed therein (see FIGS. 6A-6B).

Referring now to FIGS. 4A-4D, outer housing 300 is shown. Outer housing 300 includes a proximal end 310, a distal end 320, and a longitudinal passageway 330 extending therethrough. Longitudinal passageway 330 tapers inwardly towards the distal end 320 of outer housing 300, the importance of which will be described below. Proximal end 310 of outer housing 300 includes a pair of opposed side members 312, 314 arranged to define a generally U-shaped saddle 316 configured to receive a portion of a surgical rod 600 (FIGS. 7A-7B) therein. Outer housing 300 also includes internal threading 340 disposed within longitudinal passageway 330 towards proximal end 310 of outer housing 300. Internal threading 330, as will be described below, is configured to engage complementary threading 510 disposed on the outer periphery of set screw 500 (FIGS. 7A-7B) to engage set screw 500 (FIGS. 7A-7B) within outer housing 300, and, ultimately, to secure surgical rod 600 within U-shaped saddle 316 between V-shaped hub 220 of inner housing 200 and set screw 500 (see FIGS. 7A-7B).

Continuing with reference to FIGS. 4A-4D, outer housing 300 includes an aperture 350 defined therethrough towards distal end 320 thereof. Aperture 350 is configured to receive pin 400 which, as mentioned above, is used to facilitate securing of inner housing 200 (FIGS. 3A-3E) and outer housing 300 to one another. As best shown in FIGS. 4C-4D, outer housing further includes a pair of shelves 360, 370 on the internal surface thereof defined by longitudinal passageway 330. Shelves 360, 370 are configured to receive flanges 260, 270 of inner housing 200 (FIGS. 3A-3E) to inhibit rotation of inner housing 200 relative to outer housing 300 upon positioning of inner housing 200 therein (see FIGS. 6A-6B) and to limit movement of inner housing 200 (FIGS. 3A-3E) in an axial direction relative to outer housing 300.

Referring momentarily back to FIGS. 1A-1B, it is envisioned that the bone screw 100, e.g., shank 110 and head 120, be formed from a different material than the inner and outer housings 200, 300, respectively. More specifically, it is contemplated that shank 110 and head 120 of bone screw 100 be made from a softer material than the inner and outer housings 200, 300, respectively. For example, as mentioned above, the shank 110 and head 120 may be made from titanium or titanium alloys. The inner and outer housings 200, 300, respectively, on the other hand, may be made from cobalt chrome or a cobalt chrome alloy. Further, the inner housing 200 and outer housing 300 may be formed from different materials, e.g., one of the housings 200, 300 may be formed from cobalt chrome, while the other housing 200, 300 is formed from a cobalt chrome alloy. The set screw 500 (FIGS. 7A-7B) may likewise be formed from cobalt chrome, or a cobalt chrome alloy, similar to inner housing 200 and/or outer housing 300.

Figure 5B:
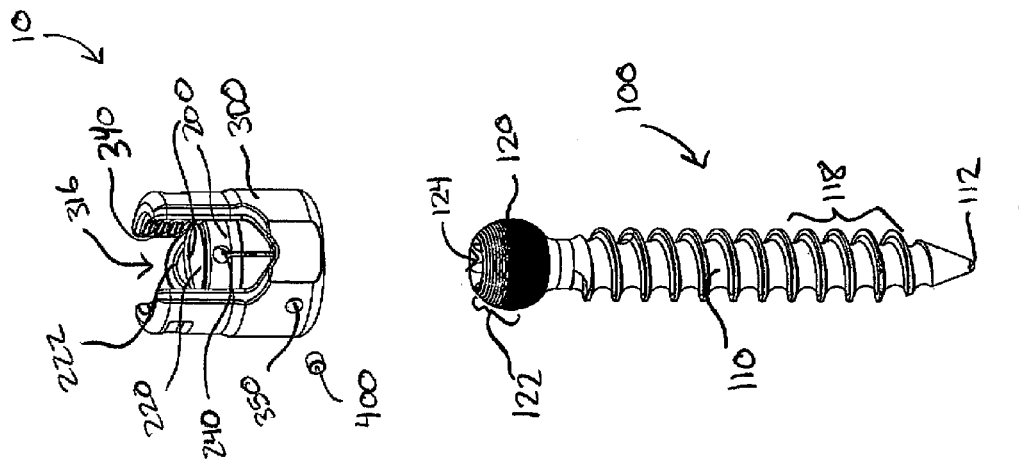
FIG. 5B is a perspective view of the bone screw assembly of FIG. 1A wherein an inner housing of the bone screw assembly has been inserted into an outer housing of the bone screw assembly.
Figure 5A:
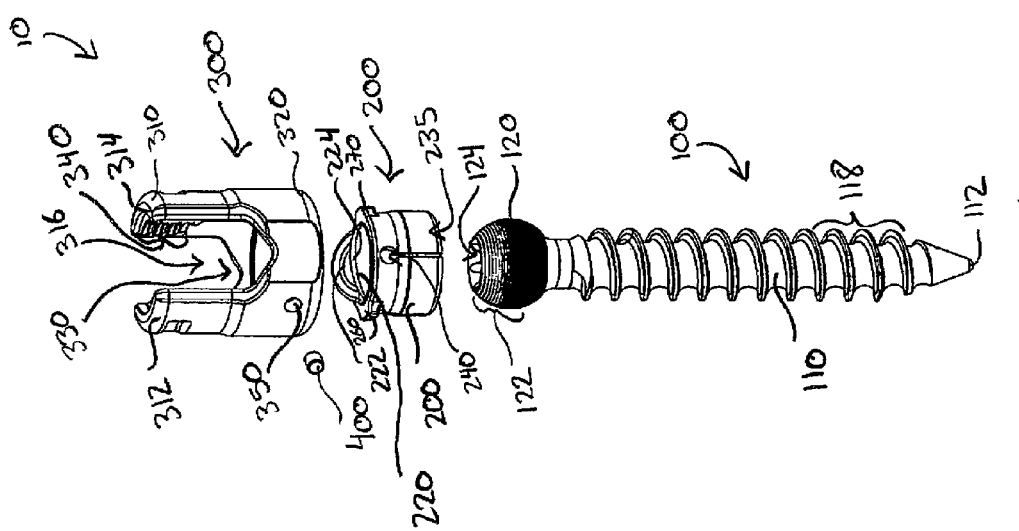
FIG. 5A is a perspective view of the bone screw assembly of FIG. 1A with parts separated.
Figure 5D:
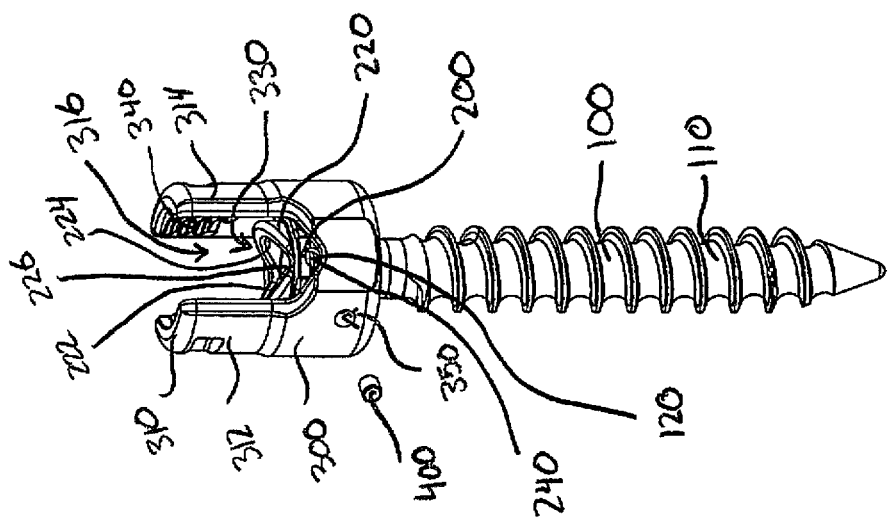
FIG. 5D is a perspective view of the bone screw assembly of FIG. 1A wherein the inner housing, the bone screw, and the outer housing are secured to one another.

Turning now to FIGS. 5A-5D, the use and assembly of bone screw assembly 10 will be described. Initially, bone screw is implanted into bone. More specifically, a drive tool (not shown) is engage within recessed proximal portion 124 of head 120 of bone screw 100 to rotationally drive bone screw 100 into bone, securing bone screw 100 therein. The bone may be pre-drilled and/or tapped prior to insertion of bone screw 100 to facilitate insertion of bone screw 100 therein. Alternatively, or additionally, as mentioned above, distal tip 112 of bone screw 100 may be self-tapping, or self-starting to facilitate insertion into bone. Next, as shown in FIG. 5B inner housing 200 is inserted into longitudinal passageway 330 of outer housing 300 from the distal end 320 of outer housing 300. In order to be received within longitudinal passageway 330 of outer housing 300, inner housing 200 is compressed (as permitted by relief features 240), e.g., the dimensions of recess 235 are contracted, allowing inner housing 200 to be positioned within longitudinal passageway 330 of outer housing 300. Upon insertion into outer housing 300, inner housing 200 is oriented relative to outer housing 300 such that flanges 260, 270 of inner housing 200 rest, or sit on shelves 360, 370, respectively, of outer housing 300 and such that slot 250 defined within inner housing 200 is aligned with aperture 350 defined within outer housing 300. As mentioned above, the engagement between flanges 260, 270 and shelves 360, 370, respectively, inhibits substantial rotation of inner housing 200 relative to outer housing 300, although some degree of rotation is still permitted. This engagement also limits axial movement of inner and outer housings 200, 300, respectively, relative to one another. The alignment between slot 250 and aperture 350 allows insertion of pin 400 therethrough, as will be described hereinbelow. Further, inner housing 200 is oriented relative to outer housing 300 such that the longitudinal axis of nadir 226 of V-shaped hub 220 of inner housing 200 is substantially aligned with U-shaped saddle 316 defined within outer housing 300, as best shown in FIG. 5D.

Figure 5C:
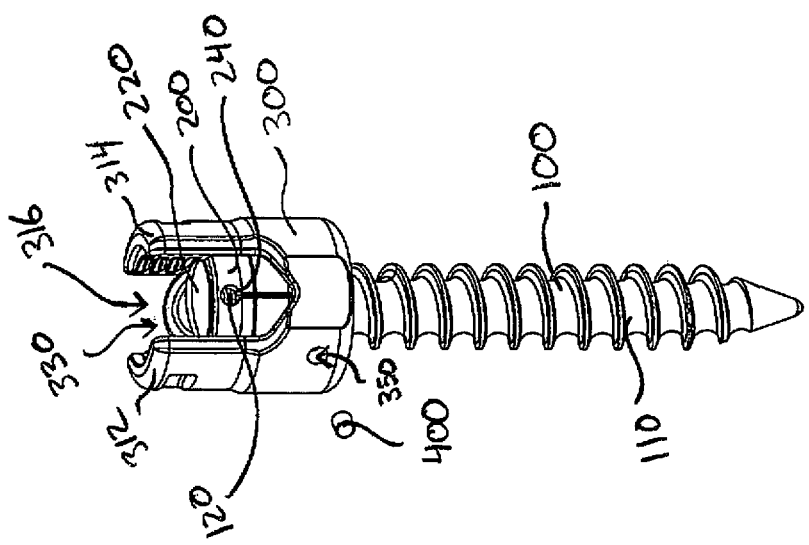
FIG. 5C is a perspective view of the bone screw assembly of FIG. 1A wherein a head of a screw of the bone screw assembly has been inserted into the inner housing.

Next, as shown in FIG. 5C, head 120 of bone screw 100 is inserted into distal recess 235 of inner housing 200. Since the semi-spherical-shaped recess 235 of inner housing 200 and the substantially spherical head 120 of bone screw 100 define approximately equal diameters, inner housing 200 is expanded, e.g., relief features 240 permit the dimensions of recess 235 to be expanded, to permit insertion of head 120 of bone screw 100 therein. Ridges 122 disposed on head 120 facilitate retention of head 120 within recess 235, while still allowing polyaxial rotation of bone screw 100 relative to inner and outer housings 200 and 300, respectively.

Figures 6A, 6B:
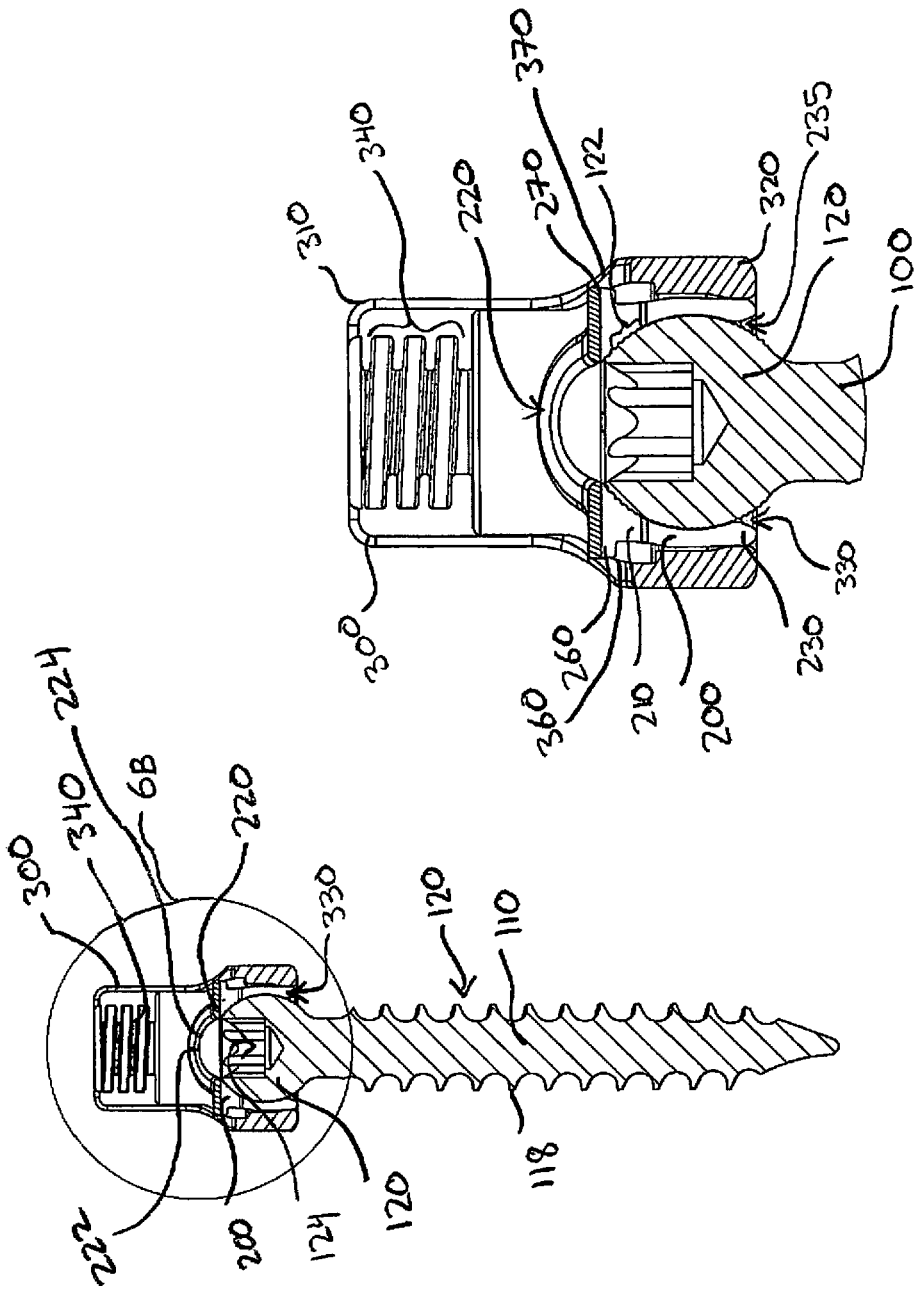
FIG. 6A is longitudinal, cross-sectional view of the bone screw assembly of FIG. 1A.
FIG. 6B is an enlarged view of the area of detail of FIG. 6A.

Referring now to FIG. 5D and FIGS. 6A-6B, with head 120 of bone screw 100 disposed within recess 235 of inner housing 200, inner housing 200 may be urged distally relative to outer housing 300. As inner housing 200 is urged distally, inner housing 200 is compressed about head 120 of bone screw 100 due to the tapered configuration of longitudinal passageway 330 of outer housing 300. In other words, as inner housing 200 is urged distally, outer housing 300 is increasingly compressed about inner housing 200 which, in turn, is compressed about head 120 of bone screw 100, thereby substantially securing outer housing 300, inner housing 200, and bone screw 100 to one another. As will be described in greater detail hereinbelow, the installation of set screw 500 (FIGS. 7A-7B) to secure surgical rod 600 (FIGS. 7A-7B) within outer housing 300 further secures, or locks outer housing 300, inner housing 200, and bone screw 100 in position relative to one another. Finally, pin 400 may be inserted through aperture 350 of outer housing 300 and slot 250 of inner housing 200 to secure inner housing 200 and outer housing 300 in position relative to one another, except for allowing translation of inner housing 200 relative to outer housing 300 the length of slot 250, e.g., pin 400 and, thus, outer housing 300 are permitted to translate relative to inner housing 200 along the length of slot 250. This range of movement of outer housing 300 relative to inner housing 200 is sufficient to reduce stresses on bone screw assembly 10 caused by manipulation of one or more of the components thereof.

Turning now to FIGS. 7A-7B, once bone screw 100 has been implanted within bone and once bone screw assembly 10 has been assembled, as described above, additional bone screw assemblies 10 may be installed and assembled similarly as described above. A surgical rod 600 may then be secured to each of the bone screw assemblies 10. More particularly, surgical rod 600 is positioned within the U-shaped saddle 316 of outer housing 300 such that surgical rod 600 is seated within V-shaped hub 220 of inner housing 200 and is secured therein via set screw 500. More specifically, surgical rod 600 is supported by first and second angled surfaces 222, 224, respectively, of V-shaped hub 220 such that, as set screw 500 is driven into engagement with outer housing 300, surgical rod 600 is urged into contact with first and second angled surfaces 222, 224, respectively, of V-shaped hub 220 which, in turn, centers surgical rod 600 relative to nadir 226 as rod 600 is urged downwardly toward nadir 226. In this position, as can be appreciated surgical rod 600 is stably and equally supported by each of first and second angled surfaces 222, 224, respectively. Set screw 500 includes threading 510, e.g., machined threading, formed about an outer periphery thereof and configured complementary to internal threading 340 of outer housing 300 such that set screw 500 may be threadingly engaged within outer housing 300 to secure surgical rod 600 therein. Set screw 500 further includes a recess 520 defined at the proximal end 530 thereof that is configured for engagement of a drive tool (not shown) therein for rotationally driving set screw 500 into engagement with outer housing 300.

The height of set screw 500 may also be chosen in accordance with the diameter of the rod 600 secured therein, such that, in a fully engaged position, regardless of the diameter of the rod 600 used, proximal end 530 of set screw 500 is substantially flush with proximal end 310 of outer housing 300, e.g., such that proximal end 330 of set screw 500 is capable of being driven to a substantially similar depth with respect to outer housing 300 regardless of the diameter of the rod 600 used therein. For example, where a larger diameter rod is used, e.g., rod 620 (FIGS. 9A-9C), set screw 500 may define a relatively shorter height, while, where a smaller diameter rod is used, e.g., rod 610 (FIGS. 8A-8C), set screw 500 may define a relatively longer height. The particular set screw 500 chosen for use with a particular rod 600 may be selected in accordance with anatomical considerations of the patient, the specific procedure to be performed, the disease/defect to be treated, etc. As such, a kit (not explicitly shown) may be provided including a plurality of set screws 500 of varying height and a plurality of rods 600 having varying diameters (e.g., different diameter rods and rods having various tapered diameters), in addition to one or more bone screw assemblies 10. Accordingly, in use, the surgeon may select the appropriate rod and set screw combination for use with the bone screw assembly (or assemblies) 10, e.g., the surgeon may select the appropriate set screw 500 such that proximal end 530 of set screw 500 may be driven to a substantially flush orientation relative to proximal end 310 of outer housing 300. Further, the kit (not explicitly shown), may provide the surgeon with the option of selecting a particular component e.g., the rod, set screw, inner housing, outer housing, bone screw, etc., formed from a particular material (or materials), e.g., titanium, titanium alloys, cobalt chrome, cobalt chrome alloys, etc. For example, the kit (not explicitly shown) may include one or more inner housings 200 made from cobalt chrome and one or more inner housings 200 made from a cobalt chrome alloy, allowing the surgeon to select the desired material. As can be appreciated, the kit (not explicitly shown) may also include material selection options for any or all of the other components.

It is also envisioned that a standard set screw 500 be provided for use regardless of the size of the rod 600. In such an embodiment, as shown in FIGS. 8C and 9C, the set screw 500 is driven to different depths depending on the diameter of the rod 600 used. In either embodiment, i.e., regardless of the height of the set screw 500, the set screw 500 is configured to exert a substantially similar force on the rod 600 when in the fully engaged position, regardless of the diameter of the rod 600 used therewith.

Set screw 500 is further configured, as mentioned above, to drive inner housing 200 downwardly into a locked position to lock inner housing 200, outer housing 300 and bone screw 100 in position relative to one another. More specifically, as set screw 500 is driven into engagement with outer housing 300, e.g., via engagement between threading 340 of outer housing 300 and threading 510 of set screw 500, surgical rod 600 is urged downwardly into proximal V-shaped hub 220 of inner housing 200. As surgical rod 600 is urged downwardly, inner housing 200 is likewise urged downwardly relative to outer housing 300. The downward urging of inner housing 200 relative to outer housing 300 causes inner housing 200 to be compressed about head 120 of bone screw 100, e.g., the dimensions of recess 235 are contracted, due to the distally tapering configuration of longitudinal passageway 330 of outer housing 300, thereby locking bone screw assembly 10 in position. Thus, engagement of set screw 500 within outer housing 300 not only secures rod 600 within bone screw assembly 10, but also locks bone screw 100, inner housing 200, and outer housing 300 in position relative to one another.

Turning now to FIGS. 8A-C and FIGS. 9A-C, the installation of rods 610, 620 of varying diameter within bone screw assembly 10 will be described to illustrate additional features of bone screw assembly 10. As shown in FIGS. 8A-8C, rod 610, having diameter "d," is secured within outer housing 300 between inner housing 200 and set screw 500. More specifically, set screw 500 have been driven into engagement with outer housing 300 to a first depth such that rod 610 is secured in position therebetween. In this position, rod 610 is centered relative to nadir 226 of proximal hub 220 and, thus, with respect to inner housing 200. Rod 610 is supported equally by first and second angled surfaces 222, 224 of proximal hub 220 and is inhibited from moving laterally therewithin.

As shown in FIGS. 9A-9C, rod 620, having diameter "D," e.g., a diameter larger than diameter "d," is secured within outer housing 300 between inner housing 200 and set screw 500. Set screw 500 have been driven into engagement with outer housing 300 to a second depth such that rod 620 is secured between proximal hub 220 and set screw 500. In this position, similar to rod 610, rod 620 is centered relative to nadir 226 of proximal hub 220 and, thus, with respect to inner housing 200. Rod 620 is likewise supported equally by first and second angled surfaces 222, 224 of proximal hub 220 and is inhibited from moving laterally therewithin. Put more generally, due to the V-shaped configuration of first and second angled surfaces 222, 224, respectively, of proximal hub 220 of inner housing 200, bone screw assembly 10 is capable of stably and securely retaining surgical rods, e.g., rods 610 and 620, of varying diameter in a centrally disposed position relative to inner housing 200, while inhibiting lateral movement of the rod 610, 620 relative to inner housing 200.

With reference now to FIGS. 10A-10C, a tapered surgical rod 700 is shown configured for use with bone screw assembly 10 (see FIGS. 1A-1B). Surgical rod 700 includes a first section 720, a second section 730, and a tapered intermediate section 740. First section 720 includes a free end 722 and a fixed end 724 and defines a generally circular cross-sectional configuration having a first diameter "DD." Second section 730 similarly includes a free end 732 and a fixed end 734 and defines a generally circular cross-sectional configuration having a second diameter "dd" smaller than the first diameter "DD." First and second sections 720, 730, respectively, are interconnected at fixed ends 724, 734, respectively, thereof via intermediate section 740. Intermediate section 740 defines a tapered configuration. More specifically, intermediate section defines a diameter similar to first diameter "DD" at first end 742 and tapers along the length thereof to second end 744 that defines a diameter similar to second diameter "dd." In other words, intermediate section 740 continuously tapers from diameter "DD" to diameter "dd" along the length thereof to interconnect first and second sections 720, 730, respectively. However, other configurations of tapered rods are also contemplated. Further, first section 720, second section 730, and intermediate section 740 may be integrally formed with one another, or may be coupled to one another in any suitable fashion.

Continuing with reference to FIGS. 10A-10C, in conjunction with FIGS. 7A-7B, as can be appreciated, due to the V-shaped configuration of proximal hub 220 of inner housing 200, bone screw assembly 10 is capable of stably and securely retaining first section 720 of surgical rod 700, having diameter "DD," as well as second section 730 of surgical rod 700, having diameter "dd." Similarly as discussed above, despite the difference in diameter, bone screw assembly 10 is adapted to retain either of first and second sections 720, 730, respectively, of surgical rod 700 in a centrally disposed position relative to inner housing 200 while inhibiting lateral movement of the rod sections 720, 730 relative to inner housing 200. In other words, the same bone screw assembly 10 may be used to secure either the first or second section 720, 730, respectively, of surgical rod 700 thereto.

It will be understood that various modifications may be made to the embodiments of the presently disclosed bone screw assembly. The aforementioned principles are applicable to any implant using a bone screw for fastening the implant to bone and/or for securing a surgical rod thereto. Therefore, the above description should not be construed as limiting, but merely as exemplifications of embodiments. Those skilled in the art will envision other modifications within the scope and spirit of the present disclosure.

What is claimed is:
1. A bone screw assembly, comprising:
   a screw having a shank and a head;
   an outer housing having a proximal end, a distal end, and a passageway extending longitudinally therethrough, the outer housing defining a saddle at the proximal end thereof for receiving at least a portion of a rod therein, the outer housing including an aperture;

an inner housing positionable within the passageway of the outer housing, the inner housing having a proximal end and a distal end, the inner housing including:

a recessed distal portion for receiving the head of the screw therein;

a V-shaped hub including a proximal surface for receiving rods of different diameters, the V-shaped hub disposed on, and extending proximally from, the proximal end of the inner housing, the V-shaped hub includes a proximal end and a distal end, the proximal end being the proximal-most end of the V-shaped hub and the distal end being the distal-most end of the V-shaped hub, the V-shaped hub including a first angled surface and a second angled surface that cooperate to define a nadir at the distal end of the V-shaped hub, the first and second angled surfaces extending at opposite angles from the nadir to the proximal end, the V-shaped hub including slits allowing the V-shaped hub to flex thereby allowing the inner housing to be inserted through an opening at the distal end of the outer housing;

a slot extending along a longitudinal axis of the inner housing; and a pin insertable through the aperture of the outer housing and receivable in the slot of the inner housing, the pin maintaining radial alignment of the inner and outer housings.

2. The bone screw assembly according to claim 1, wherein the inner housing is moveable relative to the outer housing from a proximal position to a distal position to lock the outer housing, the inner housing, and the head of the screw in position relative to one another.

3. The bone screw assembly according to claim 2, further including a set screw threadingly engageable with the outer housing, the set screw configured to secure the rod within the saddle of the outer housing between the set screw and the proximal surface of the V-shaped hub.

4. The bone screw assembly according to claim 3, wherein, as the set screw is threadingly engaged within the outer housing, the inner housing is moved relative to the outer housing from the proximal position to the distal position to lock the outer housing, the inner housing, and the head of the screw in position relative to one another.

5. The bone screw assembly according to claim 3, wherein the set screw includes machined-threading disposed about an outer periphery thereof, the machined-threading of the set screw configured to engage threading disposed on an inner surface of the outer housing.

6. The bone screw assembly according to claim 3, wherein a height of the set screw is selected in accordance with a diameter of the rod such that, in a fully engaged position, a proximal surface of the set screw is substantially flush with the proximal end of the outer housing.

7. The bone screw assembly according to claim 1, wherein at least one of the screw, the outer housing, the V-shaped hub, and the inner housing is formed from a different material.

8. The bone screw assembly according to claim 1, wherein the outer housing is made from cobalt chrome and wherein at least one of the inner housing, the V-shaped hub, and the screw is made from a different material.

9. The bone screw assembly according to claim 8, wherein the screw is made from titanium.

10. The bone screw assembly according to claim 1, wherein the screw is made from a softer material than at least one of the outer housing, the V-shaped hub, and the inner housing.

11. The bone screw assembly according to claim 1, wherein the recessed distal portion of the inner housing defines a plurality of relief features, the plurality of relief features configured to enable the recessed distal portion of the inner housing to contract upon insertion of the recessed distal portion into the outer housing and to expand upon insertion of the head of the screw in the recessed distal portion.

12. The bone screw assembly according to claim 1, wherein the head of the screw includes a plurality of circumferential ridges, the plurality of circumferential ridges configured to facilitate retention of the head of the screw within the recessed distal portion of the inner housing.

13. The bone screw assembly according to claim 1, wherein the proximal surface of the V-shaped hub is configured to receive rods having diameters in the range of about 3.5 mm to about 7 mm.

14. The bone screw assembly according to claim 1, wherein the shank of the screw is double-threaded.

15. The bone screw assembly according to claim 14, wherein a pitch of the shank is in the range of about 1 mm to about 3 mm and wherein a lead of the shank is in the range of about 2 mm to about 6 mm.

16. The bone screw assembly according to claim 14, wherein a pitch of the shank is about 2 mm and wherein a lead of the shank is about 4 mm.

17. The bone screw assembly according to claim 1, wherein an amount of relative movement between the inner and outer housings is determined by a distance the pin travels in the slot.

\* \* \* \* \*